(12) United States Patent
Russell

(10) Patent No.: US 10,947,291 B2
(45) Date of Patent: Mar. 16, 2021

(54) TREATING TYPE I AND TYPE II DIABETES

(71) Applicant: Mayo Foundation for Medical Education and Research, Rochester, MN (US)

(72) Inventor: Stephen James Russell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 258 days.

(21) Appl. No.: 15/897,030

(22) Filed: Feb. 14, 2018

(65) Prior Publication Data

US 2018/0186854 A1 Jul. 5, 2018

Related U.S. Application Data

(62) Division of application No. 14/912,443, filed as application No. PCT/US2014/052712 on Aug. 26, 2014, now abandoned.

(60) Provisional application No. 61/870,537, filed on Aug. 27, 2013.

(51) Int. Cl.
| | | |
|---|---|---|
| C07K 14/62 | (2006.01) | |
| C12N 15/85 | (2006.01) | |
| C12N 15/86 | (2006.01) | |
| C12N 9/64 | (2006.01) | |
| A61K 31/4545 | (2006.01) | |
| A61K 48/00 | (2006.01) | |
| C12N 7/00 | (2006.01) | |
| A61K 38/00 | (2006.01) | |

(52) U.S. Cl.
CPC .......... *C07K 14/62* (2013.01); *A61K 31/4545* (2013.01); *A61K 48/005* (2013.01); *C12N 7/00* (2013.01); *C12N 9/6472* (2013.01); *C12N 15/85* (2013.01); *C12N 15/86* (2013.01); *A61K 38/00* (2013.01); *C12N 2750/14143* (2013.01); *C12N 2800/90* (2013.01); *C12N 2830/20* (2013.01); *C12N 2840/203* (2013.01)

(58) Field of Classification Search
CPC .. C12N 15/86; A61K 48/005; A61K 31/4545; C07K 14/62
See application file for complete search history.

(56) References Cited

U.S. PATENT DOCUMENTS

| 7,341,869 B2 | 3/2008 | Osborne et al. |
|---|---|---|
| 2003/0113305 A1 | 6/2003 | Osborne et al. |
| 2007/0066552 A1* | 3/2007 | Clarke .................. A61K 8/606 514/44 R |
| 2011/0286980 A1* | 11/2011 | Brenner ................. A61K 35/17 424/93.21 |
| 2013/0071414 A1 | 3/2013 | Dotti et al. |
| 2013/0210897 A1* | 8/2013 | Kay ....................... C12N 15/85 514/44 R |

FOREIGN PATENT DOCUMENTS

WO WO 2012/031137 3/2012

OTHER PUBLICATIONS

Yanagita et al. (Processing of mutated proinsulin with tetrabasic cleavage sites to bioactive insulin in the non-endocrine cell line, COS-7; FEBS; vol. 311, No. 1, pp. 55-59 (1992) (Year: 1992).*
Ashcroft et al., "Diabetes mellitus and the β cell: the last ten years," *Cell.*, 148(6):1160-1171, Mar. 16, 2012.
Berenson et al., "Insulin analogs for the treatment of diabetes mellitus: therapeutic applications of protein engineering," *Ann N Y Acad Sci.*, 1243:E40-E54. Epub Mar. 13, 2012.
Callejas et al., "Treatment of diabetes and long-term survival after insulin and glucokinase gene therapy," *Diabetes*, 62(5):1718-1729, Epub Feb. 1, 2013.
Cotugno et al., "AP20187-mediated activation of a chimeric insulin receptor results in insulin-like actions in skeletal muscle and liver of diabetic mice," *Hum Gene Ther.*, 18(2):106-117, Feb. 2007.
Croze et al., "Gene therapy of streptozotocin-induced diabetes by intramuscular delivery of modified preproinsulin genes," *J Gene Med.*, 5(5):425-437, May 2003.
Delarosa et al., "Activity of the Ste20-like kinase, SLK, is enhanced by homodimerization," *Am J Physiol Renal Physiol.*, 301(3):F554-F564, Epub Jun. 15, 2011.
Di Stasi et al., "Inducible apoptosis as a safety switch for adoptive cell therapy," *N Engl J Med.*, 365(18):1673-1683, Nov. 3, 2011.
Dong et al., "Hepatic insulin expression improves glycemic control in type 1 diabetic rats," *Diabetes Res Clin Pract.*, 52(3):153-163, Jun. 2001.
Extended European Search Report in European Application No. 14/839,962.9, dated Jan. 3, 2017, 7 pages.
Gaudet et al., "Efficacy and long-term safety of alipogene tiparvovec (AAV1-LPLS447X) gene therapy for lipoprotein lipase deficiency: an open-label trial," *Gene Ther.*, 20(4):361-369, Epub Jun. 21, 2012.
Gros et al., "Insulin production by engineered muscle cells," *Hum Gene Ther.*, 10(7):1207-1217, May 1, 1999.

(Continued)

*Primary Examiner* — Antonio Galisteo Gonzalez
(74) *Attorney, Agent, or Firm* — Fish & Richardson P.C.

(57) ABSTRACT

This document provides methods and materials for treating diabetes. For example, methods and materials for using nucleic acid encoding human preproinsulin to treat diabetes (e.g., type I or type II diabetes) are provided.

11 Claims, 8 Drawing Sheets
Specification includes a Sequence Listing.

(56) References Cited

OTHER PUBLICATIONS

Hackett et al., "Efficacy and safety of Sleeping Beauty transposon-mediated gene transfer in preclinical animal studies," *Curr Gene Ther.*, 11(5):341-349, Oct. 2011.
Haddley "Alipogene tiparvovec for the treatment of lipoprotein lipase deficiency," *Drugs Today(Barc).*, 49(3):161-170, Mar. 2013.
International Preliminary Report on Patentability for PCT/US2014/052712, dated Mar. 10, 2016, 8 pages.
International Search Report and Written Opinion for PCT/US2014/052712, dated Dec. 17, 2014, 17 pages.
Kon et al., "Naked plasmid-mediated gene transfer to skeletal muscle ameliorates diabetes mellitus," *J Gene Med.*, 1(3):186-194, May-Jun. 1999.
Martinenghi et al., "Human insulin production and amelioration of diabetes in mice by electrotransfer-enhanced plasmid DNA gene transfer to the skeletal muscle," *Gene Ther.*, 9(21):1429-1437, Nov. 2002.
Mas et al., "Reversal of type 1 diabetes by engineering a glucose sensor in skeletal muscle," *Diabetes*, 55(6):1546-1553, Jun. 2006.
Nakayama, "Furin: a mammalian subtilisin/Kex2p-like endoprotease involved in processing of a wide variety of precursor proteins," *Biochem J.*, 327 ( Pt 3):625-635, Nov. 1, 1997.
Oh et al., "Gene therapy for diabetes mellitus in rats by intramuscular injection of lentivirus containing insulin gene," *Diabetes Res Clin Pract.*, 71(3):233-240, Epub Sep. 19, 2005.
Ren et al., "Long-term reversal of diabetes in non-obese diabetic mice by liver-directed gene therapy," *J Gene Med.*, 15(1):28-41, Jan. 2013.
Sadelain, "Eliminating cells gone astray," *N Engl J Med.*, 365(18):1735-1737, Nov. 3, 2011.
Short et al., "Adenovirus-mediated transfer of a modified human proinsulin gene reverses hyperglycemia in diabetic mice," *Am J Physiol.*, 275(5 Pt 1):E748-E756, Nov. 1998.
Straathof et al., "An inducible caspase 9 safety switch for T-cell therapy," *Blood.*, 105(11):4247-4254, Jun. 1, 2005.
Wong et al., "Gene therapy in diabetes," *Self Nonself.*, 1(3):165-175, Epub Jun. 9, 2010.
Xie et al., "Adenovirus-mediated tissue-targeted expression of a caspase-9-based artificial death switch for the treatment of prostate cancer," *Cancer Res.*, 61(18):6795-6804, Sep. 15, 2001.
Yanagita et al., "Processing of mutated proinsulin with tetrabasic cleavage sites to bioactive insulin in the non-endocrine cell line, COS-7," *FEBS Lett.*, 311(1):55-59, Oct. 12, 1992.
Yoon et al., "Recent advances in insulin gene therapy for type 1 diabetes," *Trends Mol Med.*, 8(2):62-68, Feb. 2002.

\* cited by examiner

SEQUENCE LISTING

```
<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: peptide

<400> SEQUENCE: 1

Lys Thr Arg Arg
1

<210> SEQ ID NO 2
<211> LENGTH: 4
<212> TYPE: PRT
<213> ORGANISM: Artificial Sequence
<220> FEATURE:
<223> OTHER INFORMATION: peptide

<400> SEQUENCE: 2

Leu Gln Lys Arg
1

<210> SEQ ID NO 3
<211> LENGTH: 4
<212> TYPE: PRT
<213> ORGANISM: Artificial Sequence
<220> FEATURE:
<223> OTHER INFORMATION: peptide

<400> SEQUENCE: 3

Arg Thr Lys Arg
1

<210> SEQ ID NO 4
<211> LENGTH: 4
<212> TYPE: PRT
<213> ORGANISM: Artificial Sequence
<220> FEATURE:
<223> OTHER INFORMATION: peptide

<400> SEQUENCE: 4

Arg Gln Lys Arg
1

<210> SEQ ID NO 5
<211> LENGTH: 47
<212> TYPE: DNA
<213> ORGANISM: Artificial Sequence
```

```
<220> FEATURE:
<223> OTHER INFORMATION: synthetically generated oligonucleotide

<400> SEQUENCE: 5
taatacgact cactataggc tagcctcgag aattcacgcg tcgagca                    47

<210> SEQ ID NO 6
<211> LENGTH: 59
<212> TYPE: DNA
<213> ORGANISM: Artificial Sequence
<220> FEATURE:
<223> OTHER INFORMATION: synthetically generated oligonucleotide

<400> SEQUENCE: 6
caacccggga tcctctagag tcgacccggg cggccgcttc cctttagtga gggttaatg     59

<210> SEQ ID NO 7
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 7
gaattcgccg ccatggccct gtggatg                                         27

<210> SEQ ID NO 8
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 8
acgcgtgctg cgtctagttg cagtag                                          26

<210> SEQ ID NO 9
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 9
tctagagcca ccatgctcga gggagtg                                         27

<210> SEQ ID NO 10
<211> LENGTH: 29
<212> TYPE: DNA
<213> ORGANISM: Artificial Sequence
<220> FEATURE:
<223> OTHER INFORMATION: synthetically generated oligonucleotide

<400> SEQUENCE: 10
gcggccgctt agtcgagtgc gtagtctgg                                       29

<210> SEQ ID NO 11
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 11
acgcgtcaat tccataccac atttg                                           25
```

<210> SEQ ID NO 12
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 12
tctagagatc ttcataagag aagag                                          25

<210> SEQ ID NO 13
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 13
ctctagagat gtacgggcca gatatac                                        27

<210> SEQ ID NO 14
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 14
ctctagactt ggaggtgcac accaatg                                        27

<210> SEQ ID NO 15
<211> LENGTH: 49
<212> TYPE: DNA
<213> ORGANISM: Artificial Sequence
<220> FEATURE:
<223> OTHER INFORMATION: synthetically generated oligonucleotide

<400> SEQUENCE: 15
ggcgcgccat atctggcccg tacatccgcg tggagctagt tattaatag                49

<210> SEQ ID NO 16
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 16
ggcgcgccga tcttcataag agaagag                                        27

TREATING TYPE I AND TYPE II DIABETES

CROSS-REFERENCE TO RELATED APPLICATIONS

This application is a divisional application of U.S. Ser. No. 14/912,443, filed Feb. 17, 2016 (Abandoned), which is a National Stage Application under 35 U.S.C. § 371 of International Application No. PCT/US2014/052712, filed Aug. 24, 2014, which claims the benefit of U.S. Provisional Application Ser. No. 61/870,537, filed Aug. 27, 2013. The disclosures of the prior applications are considered part of (and are incorporated by reference in) the disclosure of this application.

BACKGROUND

1. Technical Field

This document relates to methods and materials for treating diabetes. For example, this document provides methods and materials for using nucleic acid encoding human preproinsulin to treat diabetes (e.g., type I or type II diabetes).

2. Background Information

Insulin replacement therapy is the mainstay of treatment for all patients with type I diabetes and for many patients with type II diabetes. The goal of therapy is normoglycemia, which minimizes the risk of long-term and short-term complications, but this is rarely achieved despite multiple daily insulin injections, insulin infusion pumps, tight dietary controls, and careful insulin dose calculations based on frequent blood glucose monitoring. Inadequate insulin leads to hyperglycemia, diabetic ketoacidosis, hyperosmolar diabetic coma, and higher long-term risk of retinopathy, neuropathy, nephropathy, and cardiac, cerebral or peripheral limb ischemia. At the other extreme, excess insulin causes life-threatening hypoglycemia.

SUMMARY

This document provides methods and materials for treating diabetes. For example, this document provides methods and materials for using nucleic acid encoding human preproinsulin to treat diabetes (e.g., type I or type II diabetes). As described herein, a bicistronic construct encoding (i) a furin-activatable proinsulin and (ii) an iCasp9 inducible death switch can be designed and used to allow for pharmacological elimination of insulin-gene transduced cells if these cells overproduce insulin and cause hypoglycemia. In some cases, viral vectors such as an AAV1 vector can be used to deliver a bicistronic construct provided herein to cells (e.g., skeletal muscle cells), while nucleic acid vectors such as a naked DNA vector (e.g., a sleeping beauty vector) can be used to deliver a bicistronic construct provided herein to cells (e.g., liver cells) via, for example, hydrodynamic liver transduction. In such cases, a regulatory compound (e.g., AP1903 or AP20187) can be administered to a mammal that received a bicistronic construct provided herein if it is necessary or desirable to kill transduced cells to control insulin production and reverse, reduce, or prevent hypoglycemia. In some cases, a nucleic acid vector such as a sleeping beauty vector provided herein can be designed to be non-immunogenic and administered to the same mammal repeatedly in an effective manner without being neutralized by that mammal's immune system.

The methods and materials provided herein can allow clinicians to treat diabetes (e.g., type I or type II diabetes) using an effective insulin gene therapy approach that allows the clinician to control of the number of genetically modified insulin-producing cells, thereby ensuring that (a) an adequate quantity of insulin is produced and (b) insulin overproduction and fatal hypoglycemia are reduced or avoided. In some cases, the methods and materials provided herein can replace the daily injections of insulin (e.g., long acting insulin) used by patients with severe type II diabetes. In some cases, the methods and materials provided herein can be used to release vector-encoded insulin continuously at a steady rate, thereby providing diabetes patients with a better quality of life, better compliance with therapy, better glycemic control, lower HbA1c levels, and fewer diabetic complications.

As described herein, bicistronic AAV1 vectors and bicistronic sleeping beauty vectors can be designed and used to deliver furin-activatable human insulin to cells in vivo. For example, intramuscular delivery of AAV1 vectors encoding furin-activatable human insulin can normalize blood glucose in diabetic mice, but overdosing can cause fatal hypoglycemia. Likewise, hydrodynamic liver-directed delivery of sleeping beauty vectors encoding furin-activatable human insulin can normalize blood glucose in diabetic mice, but overdosing can cause fatal hypoglycemia. In both cases, administration of AP1903, a drug approved for clinical use, or AP20187 can quickly reverse the hypoglycemia.

In general, one aspect of this document features a nucleic acid construct comprising, or consisting essentially of, a nucleic acid encoding an insulin polypeptide and a nucleic acid encoding an inducible death switch polypeptide. The insulin polypeptide can be a proinsulin polypeptide. The insulin polypeptide can be a furin-activatable proinsulin polypeptide. The inducible death switch polypeptide can be an iCasp9 polypeptide. The construct can comprise an IRES located between the nucleic acid encoding the insulin polypeptide and the nucleic acid encoding an inducible death switch polypeptide.

In another aspect, this document features a nucleic acid vector comprising, or consisting essentially of, a nucleic acid construct comprising a nucleic acid encoding an insulin polypeptide and a nucleic acid encoding an inducible death switch polypeptide. The insulin polypeptide can be a proinsulin polypeptide. The insulin polypeptide can be a furin-activatable proinsulin polypeptide. The inducible death switch polypeptide can be an iCasp9 polypeptide. The construct can comprise an IRES located between the nucleic acid encoding the insulin polypeptide and the nucleic acid encoding an inducible death switch polypeptide. The vector can be a transposon DNA vector. The vector can be a sleeping beauty vector. The vector can be an AAV1 vector.

In another aspect, this document features a method comprising, or consisting essentially of, administering, to a mammal with diabetes, a vector comprising, or consisting essentially of, a nucleic acid construct comprising a nucleic acid encoding an insulin polypeptide and a nucleic acid encoding an inducible death switch polypeptide. The insulin polypeptide can be a proinsulin polypeptide. The insulin polypeptide can be a furin-activatable proinsulin polypeptide. The inducible death switch polypeptide can be an iCasp9 polypeptide. The construct can comprise an IRES located between the nucleic acid encoding the insulin polypeptide and the nucleic acid encoding an inducible death switch polypeptide. The vector can be a transposon DNA vector. The vector can be a sleeping beauty vector. The vector can be an AAV1 vector. The mammal can comprise type I diabetes. The mammal can comprise type II diabetes. The mammal can experience hypoglycemia, and the method can comprise administering an inducing agent to the mammal. The inducible death switch polypeptide can be an iCasp9 polypeptide, and the inducing agent can be AP1903 or AP20187.

AP1903 is a lipid-permeable tacrolimus analogue with homo-dimerizing activity and is also known as (S,2R,2'R)-(1R,1'R)-(((((ethane-1,2-diylbis(azanediyl))-bis(2-oxoethane-2,1-diyl))bis(oxy))bis(3,1-phenylene))bis(3-(3,4-dimethoxyphenyl)-propane-1,1-diyl) bis(1-((S)-2-(3,4,5-trimethoxyphenyl)butanoyl)piperidine-2-carboxylate). See, e.g., Sadelain, *N. Engl. J. Med.*, 365(18):1735-7 (2011) and Di Stasi et al., *N. Engl. J. Med.*, 365(18):1673-83 (2011). The structure for AP1903 is as follows:

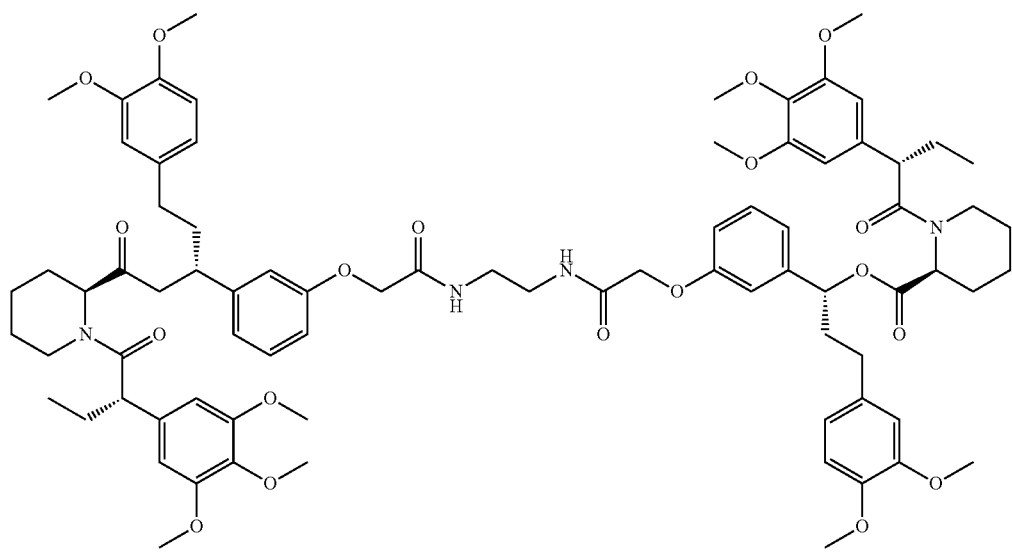 [SMILES: CC[C@H](C(=O)N1CCCC[C@H]1C(=O)C[C@H](CCc1ccc(OC)c(OC)c1)c1cccc(OCC(=O)NCCNC(=O)COc2cccc([C@@H](CCc3ccc(OC)c(OC)c3)OC(=O)[C@@H]3CCCCN3C(=O)[C@@H](CC)c3cc(OC)c(OC)c(OC)c3)c2)c1)c1cc(OC)c(OC)c(OC)c1]

AP20187 is a synthetic, cell-permeable ligand that can be used to induce homodimerization of fusion proteins containing the DmrB domain (Cotugno et al., *Hum. Gene Ther.*, 18(2):106-117 (2007) and Delarosa et al., *Am. J. Physiol. Renal Physiol.*, 301(3):F554-64 (2011)). The structure for AP20187 is as follows:

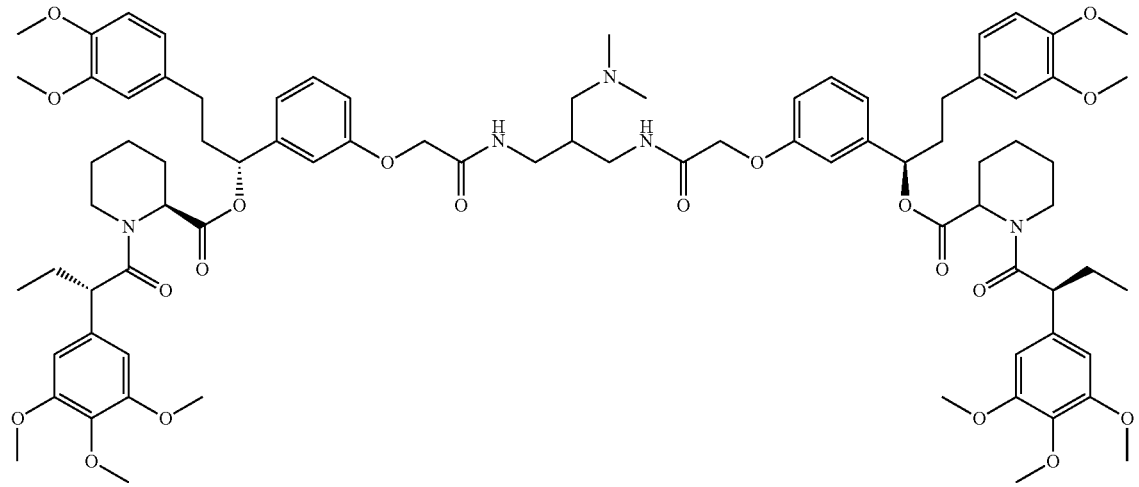

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials for treating diabetes. For example, this document provides nucleic acid vectors encoding human insulin (e.g., furin-activatable proinsulin) and an inducible cell death switch (e.g., iCasp9 inducible death switch) as well as methods for using such vectors to treat diabetes (e.g., type I or type II diabetes). As described herein, a bicistronic construct encoding (i) a furin-activatable proinsulin and (ii) an iCasp9 inducible death switch can be designed and used to express insulin within a mammal while allowing for the pharmacological elimination of insulin-gene transduced cells if these cells overproduce insulin and cause hypoglycemia.

Any appropriate nucleic acid encoding insulin can be used to make a bicistronic construct provided herein. For example, nucleic acid encoding a furin-activatable proinsulin as described elsewhere (Yanagita et al., *FEBS Lett.*, 311(1):55-9 (1992)) can be used. Other examples of nucleic acid encoding insulin can be used to make a bicistronic construct provided herein include, without limitation, nucleic acids encoding a single chain insulin or a furin activatable insulins with alternative furin cleavage signals at the BC and CA junctions as described elsewhere (Yoon and Jun, *Trends Mol. Med.*, 8(2):62-8 (2002) and Nakayama, *Biochem.*, 327(Pt 3):625-35 (1997)). In some cases, nucleic acids encoding a mutated form of insulin with altered biophysical properties such as those described elsewhere (Berenson et al., *Ann. N Y Acad. Sci.*, 1243:E40-E54 (2011)) can be used. Nucleic acid encoding such mutant forms can be converted to express furin activatable or single-chain versions of insulin and used as described herein.

Any appropriate nucleic acid encoding an inducible cell death switch can be used to make a bicistronic construct provided herein. For example, nucleic acid encoding an iCasp9 inducible death switch as described elsewhere (Xie et al., *Cancer Res.*, 61(18):6795-804 (1991) or Di Stasi et al., *N. Engl. J. Med.*, 365(18):1673-83 (2011)) can be used.

Figure 3:
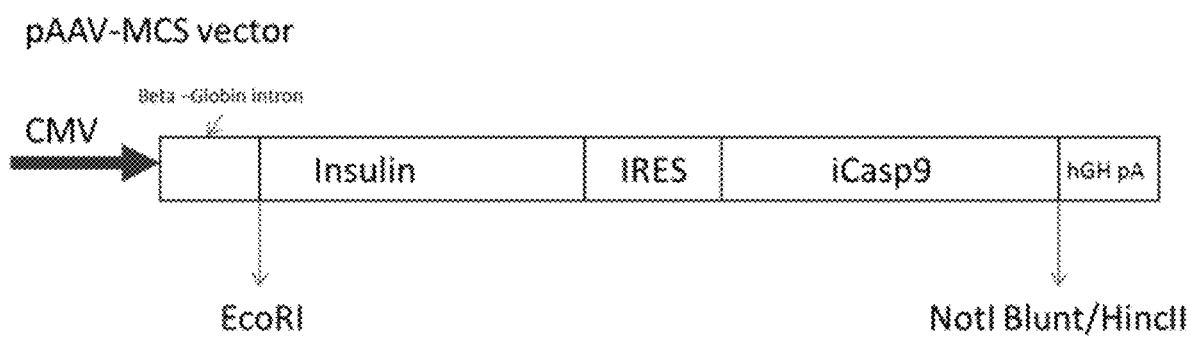
FIG. 3 is a schematic representation of a bicistronic construct encoding (i) a furin-activatable proinsulin and (ii) an iCasp9 inducible death switch.

In some cases, a bicistronic construct provided herein can include one or more promoter sequences operably linked to a polypeptide-encoding sequence, one or more enhancers, one or more transcription termination signals, and/or one or more internal ribosome entry sites (IRES's). For example, a bicistronic construct provided herein can be designed as shown in FIG. 3. Examples of promoter sequences include, without limitation, constitutive promoter sequences, CMV promoter sequences, chicken beta actin promoter sequences, SFFV promoter sequences, glucose responsive promoter sequences, L-type pyruvate kinase (LPK) promoter sequences, Spot 14 promoter sequences, muscle specific promoter sequences (e.g., myosin promoter sequences), sarcoglycan promoter sequences, liver specific promoter sequences, albumin promoter sequences, and alpha 1 antitrypsin promoter sequences.

A bicistronic construct provided herein can be part of a nucleic acid vector (e.g., a naked DNA sleeping beauty vector) or can be incorporated into a viral vector. Such vectors can be designed to express the insulin-encoding sequence once the vector is introduced into cells. Suitable examples of expression vectors include, without limitation, plasmids and viral vectors derived from, for example, sleeping beauty transposons, piggyBac transposons, EBV replicons, bacteriophage, baculoviruses, tobacco mosaic virus, herpes viruses, cytomegalovirus, retroviruses, lentiviruses, poxviruses, adenoviruses, and adeno-associated viruses. In some cases, an expression vector that is non-immunogenic can be used to introduce a bicistronic construct provided herein into cells within a mammal. Examples of such non-immunogenic expression vectors include, without limitation, naked DNA sleeping beauty vectors, piggyBac transposons, and EBV replicons.

In some cases, an expression vector can include a tag sequence designed to provide information about the expression vector's activity and/or location. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with an encoded polypeptide. Such tags can be inserted anywhere within the polypeptide including at either the carboxyl terminus or amino terminus. In some cases, an expression vector can include a tag sequence that is not part of a fusion polypeptide with the expressed insulin polypeptide. For example, nucleic acid encoding a sodium-iodide symporter (NIS) can be incorporated into a vector that includes a bicistronic construct provided herein to provide a manner for assessing the vectors activity and/or location within a mammal using ligands recognized by NIS such as radioiodine, pertechnetate, or tetrafluoroborate as described elsewhere (International Patent Application No. PCT/US2011/050227).

Any appropriate method can be used to insert nucleic acid (e.g., a bicistronic construct provided herein) into a naked DNA vector (e.g., a sleeping beauty vector) or the genome of a viral vector (e.g., a AAV1 vector). For example, standard molecule biology techniques such as restriction enzyme cutting, ligations, and homologous recombination can be used to insert nucleic acid into a vector. Any appropriate method can be used to identify vectors containing a bicistronic construct. Such methods include, without limitation, PCR and nucleic acid hybridization techniques such as Northern and Southern analysis. In some cases, immunohistochemistry and biochemical techniques can be used to determine if a viral vector contains a bicistronic construct by detecting the expression of an insulin polypeptide encoded by that bicistronic construct.

A vector provided herein (e.g., a nucleic acid vector that includes a bicistronic construct provided herein or a viral vector that includes a bicistronic construct provided herein) can be formulated as a pharmaceutical composition by admixture with pharmaceutically acceptable non-toxic excipients or carriers. Such compositions can be administered to a subject in need thereof in an amount effective to treat, for example, diabetes (e.g., type I or type II diabetes). Pharmaceutical compositions can be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration can be prepared as desired using appropriate methods.

In some cases, a transposon DNA vector (e.g., a sleeping beauty vector) can be delivered to the liver by hydrodynamic infusion through the hepatic venous circulation. Hydrodynamic delivery can be accomplished either by using a double-balloon catheter introduced into the inferior vena cava from the femoral vein for infusion into the whole liver, or by using a single balloon catheter introduced into the left hepatic vein from the jugular vein for infusion into the left lobes of the liver. A DNA-containing solution (200 mL) can be infused either at a set rate of 18 to 20 mL/sec or at an increasing rate of 0 to 40 or 0 to 50 mL/sec, resulting in peak levels of expression 1 to 7 days post-infusion. Without additional treatments, reporter gene product (e.g., a secreted alkaline phosphatase) in the peripheral blood can decline to undetectable levels 42 days post-infusion.

After administration of a vector provided herein, the mammal (e.g., human diabetic patient) can be monitored for insulin over-production and/or hypoglycemia. If either or both are detected or suspected, then a compound capable of inducing the inducible cell death switch (e.g., iCasp9 inducible death switch) to kill cells expressing insulin from the administered vector can be administered to the mammal to kill at least a portion of those cells (e.g., at least about 25, 50, 75, 85, 90, 95, 99, or 100 percent of those cells). Treatment with such an agent can result in a reduction in insulin production (e.g., a rapid reduction in insulin production) and/or a reduction in hypoglycemia (e.g., a rapid reduction in hypoglycemia).

iCasp9 is an example of a suitable inducible cell death switch that can be used as described herein with its corresponding inducing agent, AP1903 or AP20187.

The invention will be further described in the following examples, which do not limit the scope of the invention described in the claims.

EXAMPLES

Example 1

Insulin Gene Therapy for Diabetes

Figure 1:
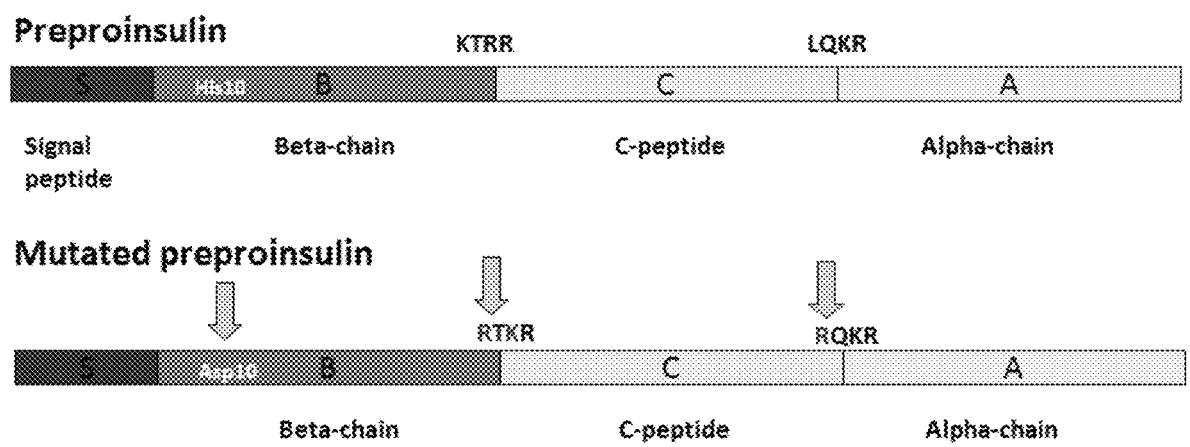
FIG. 1 is a schematic representation of preproinsulin and a mutated preproinsulin. Furin-cleavable sites were inserted at B-chain/C-peptide and A-chain/C-peptide junctions. KTRR (SEQ ID NO:1), LQKR (SEQ ID NO:2), RTKR (SEQ ID NO:3), and RQKR (SEQ ID NO:4) are amino acid sequences. His10 was changed to Asp10 in B-receptor to increase stability and affinity of insulin for its receptor to enhance biological potency.

Nucleic acid encoding human preproinsulin was designed such that the proprotein convertase cleavage signals at the B/C and C/A peptide junctions were modified to allow recognition and cleavage by furin, which is present in the Golgi compartment of most mammalian cells. Briefly, the B/C and C/A cleavage signals were mutated, respectively, from KTTR to RQKR and from LQKR to RQKR (FIG. 1). As a result of these modifications, the expressed preproinsulin polypeptide is processed to functional insulin in the Golgi apparatus of most mammalian cell types and then released by the cell into the extracellular medium.

Figure 2:
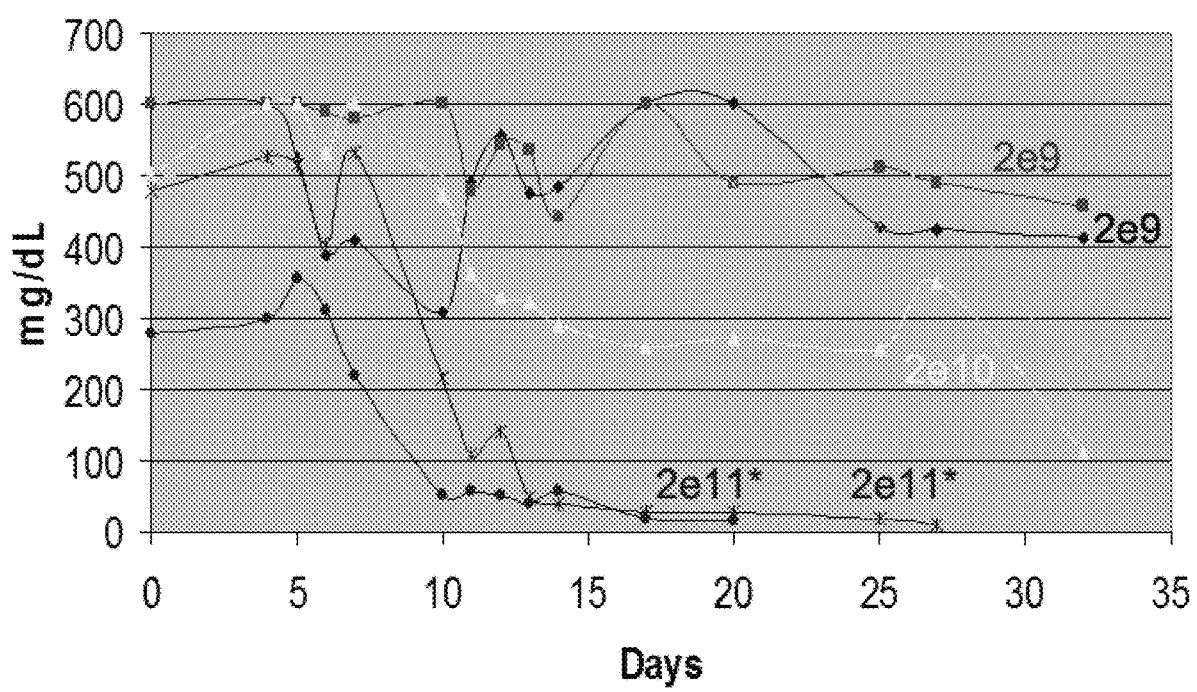
FIG. 2 is a graph plotting glucose levels (mg/dL) in blood of diabetic mice after treatment with an AAV1-insulin vector at the indicated doses. A dose of 2e9 virus particles was too low and not effective, while a dose of 2e11 virus particles was too high as high levels of insulin resulted in hypoglycemia and death.

Initially, AAV1 or sleeping beauty (SB) vectors encoding a furin-activatable proinsulin without an iC9 death switch were used (FIG. 1). Intramuscular administration of the AAV1-insulin vector to mice with streptozotocin-induced diabetes led to a dose-dependent reduction in the blood glucose level, but caused fatal hypoglycemia at higher doses (FIG. 2). Likewise, hydrodynamic delivery of the SB-insulin construct depressed blood glucose, but caused fatal hypoglycemia at higher doses.

Figure 4:
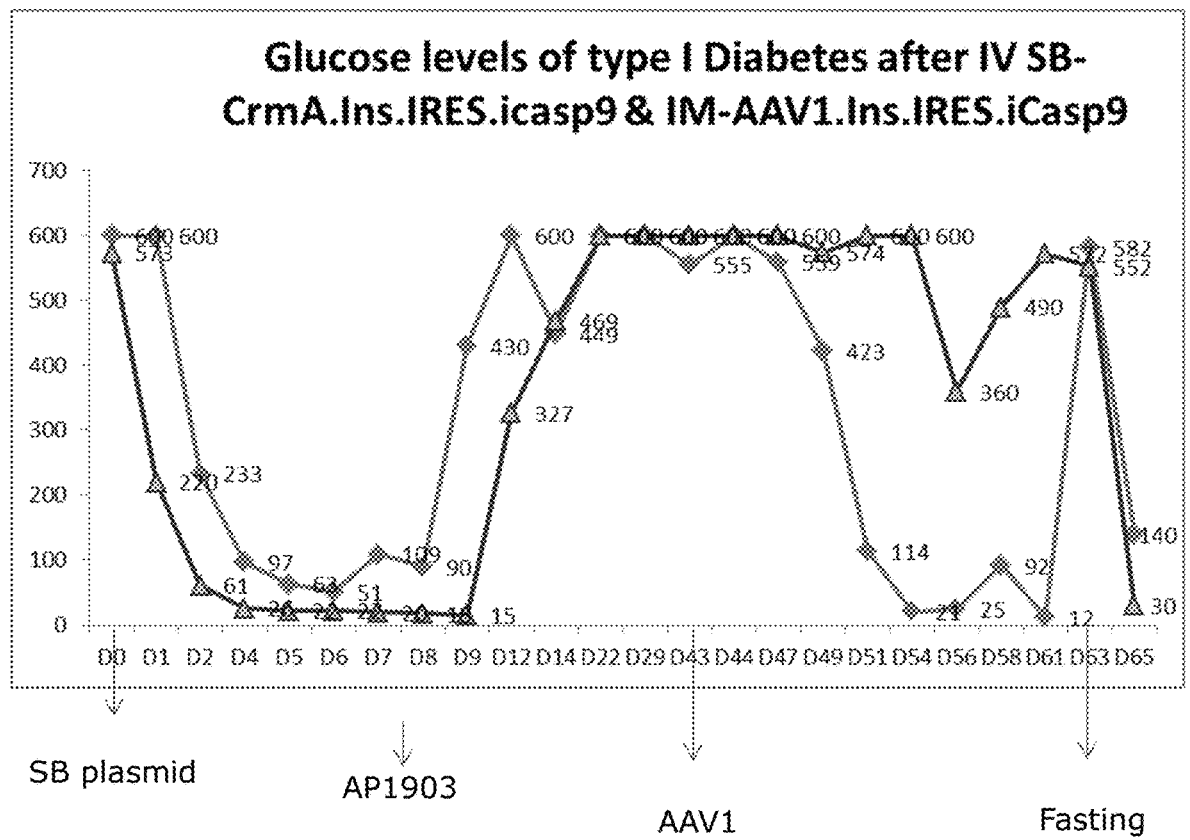
FIG. 4 is a graph plotting glucose levels for two representative mice treated with a bicistronic sleeping beauty vector, followed by administration of AP1903, followed by administration of a bicistronic AAV1 vector, followed by fasting.

In addition, AAV1 and SB plasmid vectors were designed to encode two polypeptides: a furin-activatable proinsulin and an iCasp9 inducible death switch that allows for the pharmacological elimination of insulin-gene transduced cells (FIG. 3). More than 200 diabetic mice were treated to optimize the protocol. Briefly, hydrodynamic delivery of the bicistronic SB vectors and intramuscular delivery of the biscistronic AAV1 vectors dramatically reduced the blood glucose levels in spontaneously diabetic NOD mice. Moreover, the life threatening hypoglycemia that subsequently developed in these animals was rapidly and completely reversed by subsequent administration of AP1903, the iC9 dimerizing drug. A representative dataset from two mice is shown in FIG. 4.

Since human patients given intramuscular AAV1 vectors can develop anti-AAV1 antibodies, passively administered anti-AAV antibodies were tested to determine whether they could block the transduction of muscle cells upon AAV vector re-administration. The data indicated that repeat dosing with AAV1-insulin vectors may be neutralized by anti-AAV antibodies.

These results demonstrate that vectors such as non-immunogenic vectors (e.g., a SB vector) can be used to deliver nucleic acid encoding furin-activatable proinsulin and a death switch polypeptide (e.g., an iC9 death switch polypeptide) to cells within a mammal once or in a repeatable manner that results in decreased glucose levels.

Example 2

Safety Studies of AAV-Insulin-iC9 in Mice

The optimal vector dose is determined in mice. Experimental diabetes is induced in 8-week-old C57Bl/6 mice by multiple intraperitoneal injections of streptozotocin (50 mg/kg) resuspended in 0.1 M citrate buffer (pH 4.5) over the course of five days. Fasting blood glucose levels are monitored bi-weekly by FreeStyle Lite Blood Glucose Monitor (Abbott, Ill., USA). Two weeks after diabetes induction, groups of diabetic mice (n=6) receive increasing doses of AAV1-INS-iCasp9 ($2.5 \times 10^{11}$, $5 \times 10^{11}$, $1 \times 10^{12}$, $2 \times 10^{12}$, $4 \times 10^{12}$, $8 \times 10^{12}$, $1.6 \times 10^{13}$, and $3.2 \times 10^{13}$ vg/kg in 200 µL of saline) distributed into tibialis cranealis, gastrocnemius and quadriceps muscles of both hindlimbs. Control groups are non-STZ-treated and STZ-treated mice treated with saline. The mice are monitored for body weight, plasma insulin, c-peptide, and blood glucose levels in the morning and evening and glucose responsiveness through glucose challenge for four weeks after AAV1 administration. After euthanasia of the mice, the beta-cell mass is examined, and muscle insulin expression is determined by immunohistochemistry.

Using the optimal AAV1 vector dose determined in the dose escalation study, the pharmacodynamics of AAV1-Ins-iCasp9 vector treatment and AP1903-mediated elimination of the vector-infected cells is determined. Diabetic mice are treated with test or control (AAV1-luciferase) vectors with or without subsequent AP1903 treatment 10 days after vector administration. 12 groups of mice (n=40 for groups 1-6, n=30 for groups 7-12) are used.

Body weights, blood glucose levels, and glucose excursion after glucose challenge are monitored at weekly intervals. A subset of mice from each group are euthanized at 3 days, 21 days, and 90 days after vector administration for organ histology, analysis of injected muscle, and determination of AAV1 vector biodistribution. Blood is analyzed at each of these time points for hematological parameters (VetScan HM2 Hematology System; 50 µL blood in EDTA for WBC counts, WBC histogram, Hb, Hct, MCV, MCH, MCHC, RDW, graphic RBC histogram, PLT count, MPV, PCT, PDW and Graphic platelet histogram) and chemistry (VetScan Classic; 100 µL blood in lithium heparin; ALB, ALP, ALT, AMY, BUN, CA++, CRE, GLOB, GLU, K+, Na+, PHOS, TBIL, TP), as well as measurements of plasma insulin and C-peptide.

At sacrifice, various tissues (e.g., hind limbs, brain, heart, lung, liver, kidney, spleen, and pancreas) are harvested to analyze the pathology, influence on pancreatic beta cells, AAV1 vector genome biodistribution, and insulin or luciferase expression. Intramuscular insulin or luciferase expression is examined by immunohistochemistry, while biodistribution of AAV1 vector is assessed by determination of vector genome copy numbers in the DNA samples by real-time PCR. Possible vector-mediated induction of antibodies against AAV1 vector components, insulin, and iCasp9 proteins are determined by AAV1 neutralization assay and Western blotting. These studies are used to assess toxicity and to determine an appropriate concentration of AAV1 vectors to be used for a large animal model and humans.

Example 3

Safety Studies of AAV-Insulin-iC9 in Non-Human Primates

Cynomolgus macaques are exposed to streptozotocin (STZ) for diabetes induction followed by disease characterization and then application of AAV1-insulin-iC9 gene therapy for safety and efficacy evaluations. All animals are euthanized at the completion of study and undergo full necropsy. In both the pre and post-STZ phase, animals are screened for baseline characteristics including CBC, chemistry (CPK inclusion required), and HA1c. Blood glucose is measured at least twice daily in the morning (pre prandial) and evening (post prandial). A metabolic panel including c-peptide, IVGTT, AST, MMTT, and 8 hour standard glucose curve is performed. AAV1-ins-IC9 is administered by multiple intramuscular injections unilaterally in the leg muscle under general anesthesia. Dosing is as follows (in genome copies per kilogram): 10e12 (NHP #1), 2×10e12 (NHP #2), or 4×10e12 (NHP #3) using a Quadra-Fuse needle (or equivalent) injection device at a standard concentration of 10e12 genomes in 1 mL of saline per injection. Treatment is applied in a single session, based on dose and intended delivery site (upper thigh). The recipient is subjected to 10-40 injections.

Safety and efficacy are evaluated at regular intervals to include CBC, chemistry (CPK inclusion required), and HA1c. An immune panel to include serum anti-AAV1 antibody titers and standard cytokine panel (G-CSF, GM-CSF, IFNγ, IL-β, IL-1ra, IL-2, IL-4, IL-5, IL-6, IL-8, IL-10, IL-12/23(p40), IL-13, IL-15, IL-17A, MCP-1, MIP-1βMIP-1α, sD40L, TGF-α, TNF-α, VEGF, and IL-18) is used. A metabolic panel including c-peptide, IVGTT, AST, MMTT, and 8 hour standard glucose curve is performed. CBC/Chem is evaluated day 0, then biweekly starting on day 7. Serum CPK is measured d0, 1, 2 to assess muscle damage potential post injection, then biweekly as part of the chemistry panel. Immune panel is evaluated on days 0, 7, 14, 21, 28, and 90 and includes serum anti-AAV1 antibody titers (in vivo mouse protection assay) and standard cytokines. Blood glucose is measured at least twice daily in the morning (pre prandial) and evening (post prandial). An 8 hour standard glucose curve is obtained on days 1-7 (week1), week 4, and week 12. MMTT is performed on days 15, 45, and 75, and IVGTT is performed on days 30 and 90. C-peptide levels are obtained weekly. If dangerous hypoglycemia occurs or if increasingly frequent severe hypoglycemia occurs that cannot be managed by insulin adjustments, then AP 1903 (Bellicum Pharmaceuticals, 0.4 mg per kg as a 2 hour infusion) is administered to terminate gene expression, and the participant is followed up for any evidence of adverse effects related to the trial or gene termination procedure.

Example 4

Safety Studies of SB-Insulin-iC9

Trials similar to those described in Examples 2 and 3 are conducted to assess the safety of SB vectors having nucleic acid encoding insulin and iC9 with some differences, including the different time courses of expression. There is a delayed onset of expression after AAV administration, while after hydrodynamic delivery there is a large burst of expression followed by fall-off to a new steady-state level. Briefly, STZ induced cynomolgous macaques about 5 kg weight are hydrodynamically infused with Insulin-iCasp9 transposon plus SB100× transposase DNA under general anesthesia using single- or double-balloon catheters placed in the inferior vena cava or the left hepatic vein, respectively, under fluoroscopic guidance. Initial transposon/transposase dosing is based on results from mouse dose-response studies that are predicted to yield an insulin expression level that is effective in treating STZ-induced diabetes in the non-human primates while at the same time unlikely to trigger critical hypoglycemia. Animals are tracked closely for levels of insulin and glucose as well as liver transaminases (as a sign of damage) and cytokines as readouts for adverse immune responses. An extended expression of insulin is possible based on the ability of the SB transposon system to mediate chromosomal integration, although there may be a reduced level of expression observed over time. These animals are then given a second treatment, perhaps at higher Insulin-iCasp9 transposon dose, especially if the initial dose is less than effective. Subsequent animals are started at the higher, more effective dose to test reproducibility of that dose.

Example 5

Insulin Gene Therapy for Diabetes

Plasmids and Vectors

Template DNA was amplified via PCR from insulin, iCasp9, SV40 polyA, and RSV promoter expression constructs using Platinum Taq (Invitrogen, Carlsbad, Calif., USA) as per the manufacturer's instructions with the following pairs of primers:

For the insulin sequence:

```
EcoRI INSULINsen
                                    (SEQ ID NO: 7)
5'-GAATTCGCCGCCATGGCCCTGTGGATG-3'

MluINSULINanti
                                    (SEQ ID NO: 8)
5'-ACGCGTGCTGCGTCTAGTTGCAGTAG-3'
```

For the iCasp9 sequence:

```
XbaIICASP9sen
                                    (SEQ ID NO: 9)
5'-TCTAGAGCCACCATGCTCGAGGGAGTG-3'

NotICASP9anti
                                    (SEQ ID NO: 10)
5'-GCGGCCGCTTAGTCGAGTGCGTAGTCTGG-3'
```

For the polyA sequence:

```
MluPOLYAsen
                                    (SEQ ID NO: 11)
5'-ACGCGTCAATTCCATACCACATTTG-3'

XbaPOLYAanti
                                    (SEQ ID NO: 12)
5'-TCTAGAGATCTTCATAAGAGAAGAG-3'
```

For the RSV promoter sequence:

```
XbaRSVsen
                                    (SEQ ID NO: 13)
5'-CTCTAGAGATGTACGGGCCAGATATAC-3'

XbaRSVanti
                                    (SEQ ID NO: 14)
5'-CTCTAGACTTGGAGGTGCACACCAATG-3'
```

For the CMV promoter to polyA sequence:

```
AscCMV.sen
                                    (SEQ ID NO: 15)
5'-GGCGCGCCATATCTGGCCCGTACATCCGCGTGGAGCTAGTTA-
TTAATAG-3'

AscPOLYAanti
                                    (SEQ ID NO: 16)
5'-GGCGCGCCGATCTTCATAAGAGAAGAG-3'
```

Figure 5A:
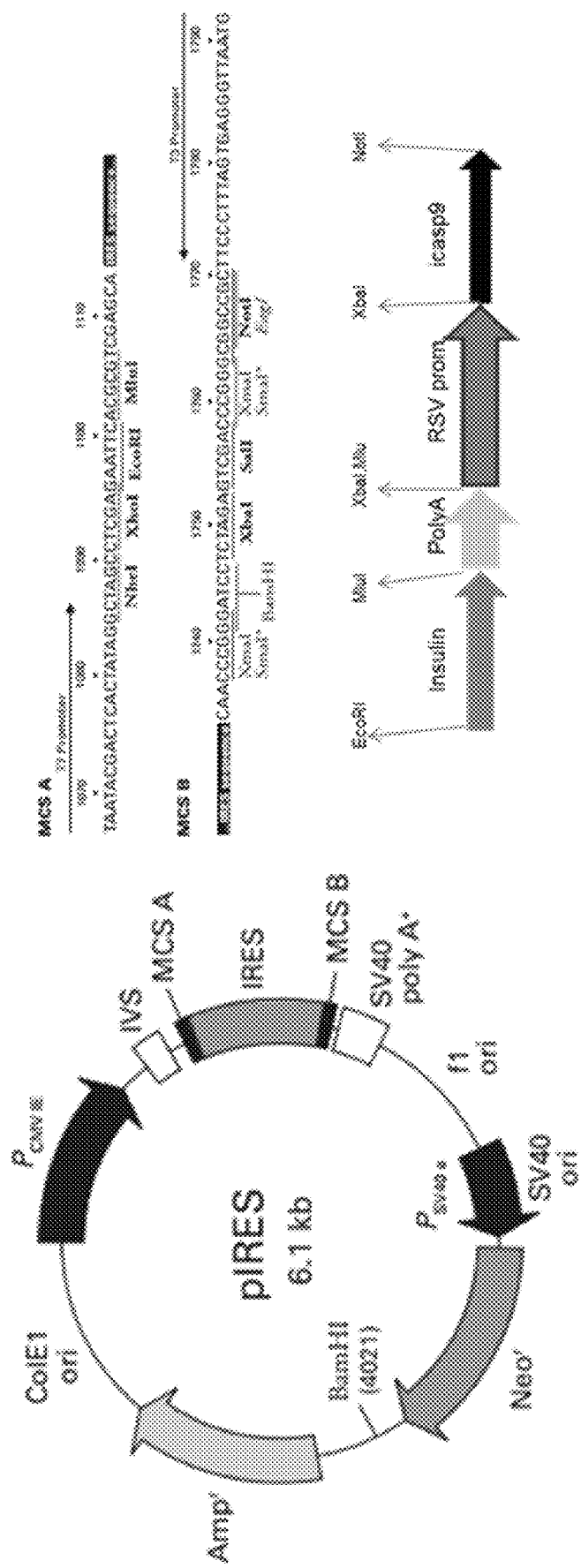
FIGS. 5A-5C are diagrams of a cloning process for making an AAV1 vector having nucleic acid encoding an insulin polypeptide under the control of a CMV promoter sequence and nucleic acid encoding an iCasp9 polypeptide under the control of an RSV promoter. A portion of multiple cloning site A (SEQ ID NO:5) and multiple cloning site B (SEQ ID NO:6) is shown in FIG. 5A.
Figure 5B:
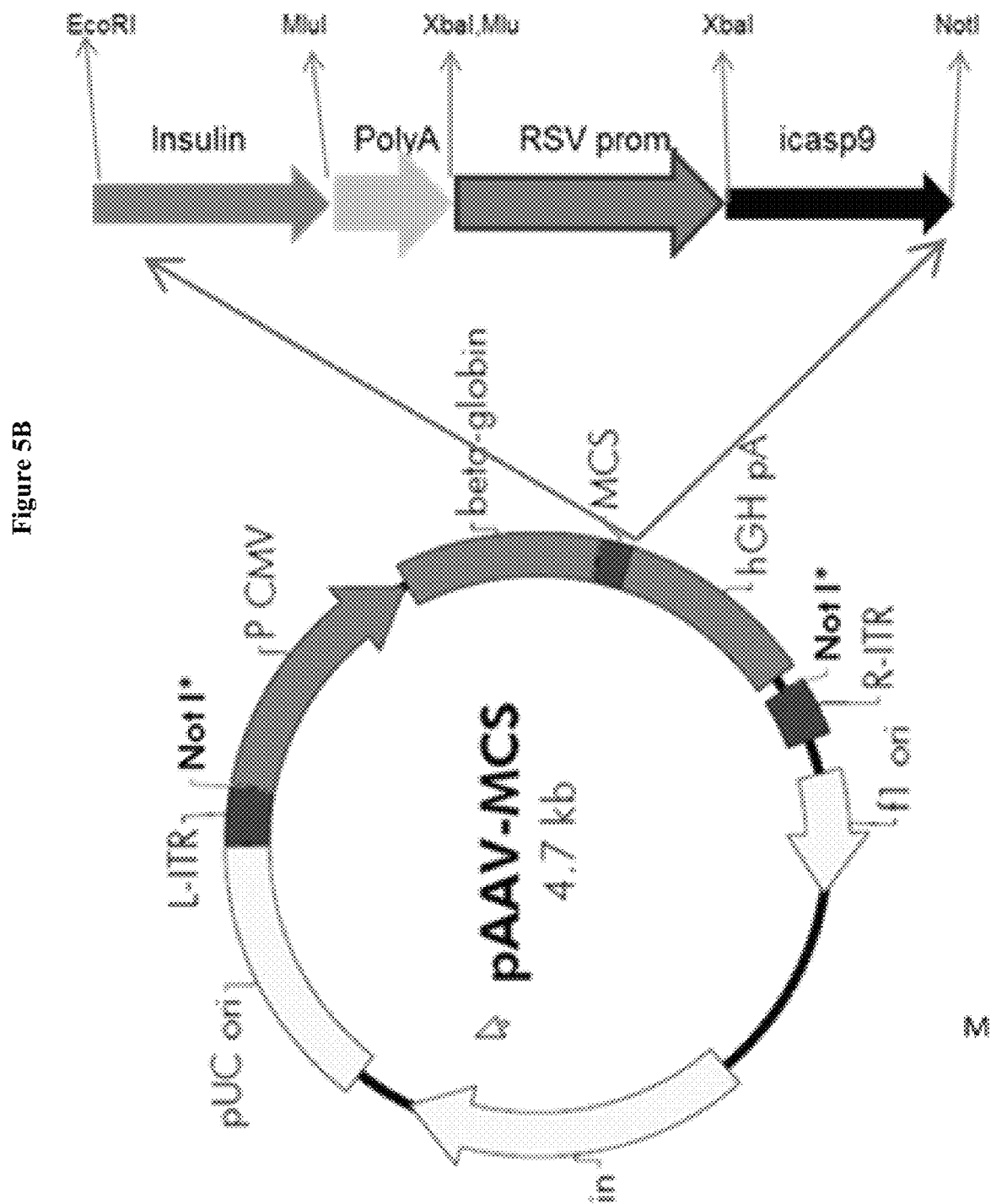
Figure 5C:
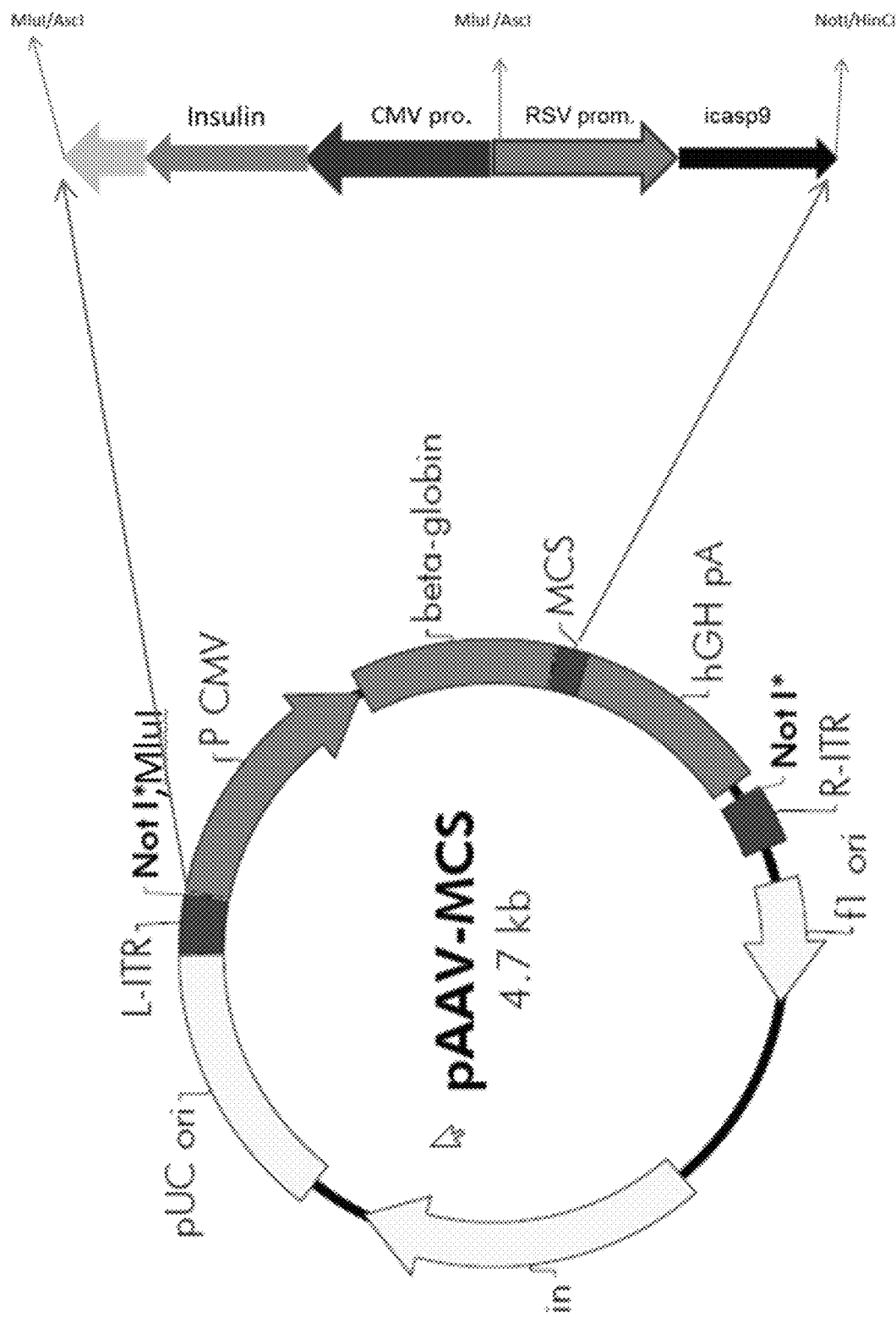

As shown in FIGS. 5A-5C, the result PCR products were cloned into the pCR2.1 vector (Invitrogen, Carlsbad, Calif., USA) using a TOPO TA cloning kit. The plasmids pCR2.1-insulin (from Fatima Bosch), pCR2.1-iCASP9 (plasmid 1567 addgene.org), pCR2.1-PolyA (SV40 polyA), pCR2.1-RSV (Invitrogen cat #V780-20), and pCR2.1-CMV.insulin.polyA were verified by sequencing. pCR2.1-insulin was digested with EcoRI and Mlu. pCR2.1-icasp9 was digested with XbaI and NotI and then gel purified and ligated into the EcoRI/MluI and XbarNotI site of the pIRES (Clontech cat #631605) shuttle vector. pCR2.1-polyA was digested with MluI and XbaI. pCR-RSV was digested with XbaI and then gel purified and ligated into MluI/XbaI of pIRES-insulin.i-casp9 vector. The shuttle vector was then digested with NotI site, blunted, digested with EcoRI, and then ligated to pCMV-MCS (AAV Helper free system, Stratagene). This vector was digested with MluI, and the insert digested with AscI was ligated into pCR2.1-CMV.insulin.polyA. This PCR product was amplified from shuttle vector to make pCMV.insulin-RSV.iCasp9.

AAV1-insulin-icasp9 vector stocks were prepared by cotransfection of plasmids pAAV-insulin.icasp9, pAAV-Rep2Cap1 (from Fatima Bosch), and pHelper (Stratagene) in 293-T cells using PEI transfection reagent. 72 hours later, cells were lysed by repeated freeze thawing (3 cycles), and the crude lysate was clarified by centrifugation at 9000 rpm for 10 minutes. Released AAV vector particles were purified on discontinuous iodixanol step gradients. Briefly, iodixanol step gradients were formed in quick-seal centrifuge tubes (25×59 mm, Beckman cat #342414) by underlaying and displacing the less dense cell lysate with iodixanol prepared using a 60% (w/v) solution of Optiprep (Sigma D1556-250 ml) and phosphate buffered saline buffer. Each gradient consisted of 5 mL 54%, 5 mL 40%, 6 mL 25%, and 9 mL 15% iodixanol. Tubes were sealed and centrifuged at 63,000 rpm for 2 hours at 15° C. Approximately 3 mL of 54%-40% interface was aspirated from each tube using an 18-guage needle. Iodixanol bands were combined, desalted, and concentrated using Amicon Ultra-15 centrifugal filter devices (Millipore #UFC910024). Final vector stocks were titrated by quantitative PCR and were expressed as AAV genome copy number per mL.

In Vivo Experiment

To induce diabetes in mice, three groups of female mice (C57/BL6) were given, on 5 consecutive days, an intraperitoneal (IP) injection of Streptozocin (STZ; Sigma cat #50130) at 45 mg/kg body weight dissolved in 0.1 mol/L citrate buffer (pH 4.5) immediately before administration. Two weeks later, when hyperglycemia developed, two groups of mice were injected intramuscularly (IM) with 1×10E11 particles/mice of AAV1.CMV.insulin.RSV.icasp9. Blood glucose levels were determined using a Contour blood glucose test strips (Bayer HealthCare LLC). 14 days later, one group of mice was injected via IP injection with 10 mg/kg of AP20187 (B/B homodimerizer; Clontech, Cat. No. AP20187) for 5 consecutive days.

Figure 6:
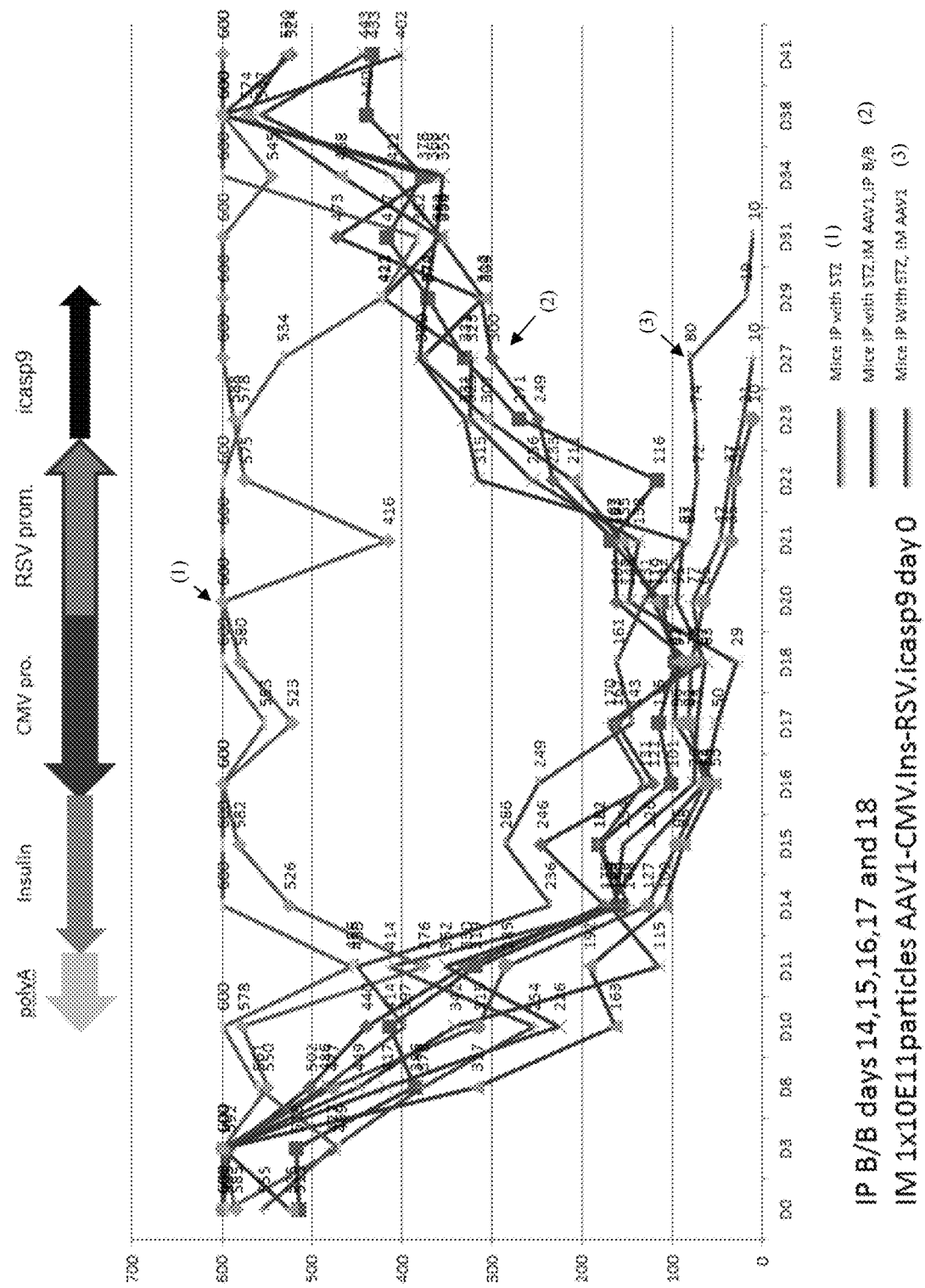
FIG. 6 is a graph plotting glucose levels for three groups of mice. One group was treated intraperitoneally (IP) with streptozocin (STZ) for two weeks to develop hyperglycemia. A second group was treated intraperitoneally (IP) with streptozocin (STZ) for two weeks to develop hyperglycemia and then administered AAV1.CMV.insulin.RSV.icasp9 (AAV1) intramuscularly (IM) on day zero. The third group was treated intraperitoneally (IP) with streptozocin (STZ) for two weeks to develop hyperglycemia, was then administered AAV1.CMV.insulin.RSV.icasp9 (AAV1) intramuscularly (IM) on day zero followed by intraperitoneal (IP) administration of AP20187 (B/B) on days 14, 15, 16, 17, and 18.

All mice injected with streptozocin developed elevated glucose levels (FIG. 6). IM administration of AAV1.CMV.insulin.RSV.icasp9 on day zero resulted in a steady reduction in glucose levels (FIG. 6). Five consecutive days of IP administration of AP20187 starting on day 14 resulted in a steady increase in glucose levels (FIG. 6). These results demonstrate that delivery of nucleic acid encoding an insulin polypeptide and an inducible death switch polypeptide can be used to reduce glucose levels within mammals having elevated glucose levels. These results also demonstrate that induction of the inducible death switch polypeptide can allow for the pharmacological elimination of insulin-gene transduced cells if these cells overproduce insulin and cause hypoglycemia.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating diabetes, wherein said method comprises administering, to a mammal with diabetes, a vector comprising a nucleic acid construct comprising a nucleic acid encoding an insulin polypeptide and a nucleic acid encoding an inducible death switch polypeptide.

2. The method of claim 1, wherein said mammal comprises type I diabetes.

3. The method of claim 1, wherein said mammal comprises type II diabetes.

4. The method of claim 1, wherein said mammal experiences hypoglycemia, and said method comprises administering an inducing agent to said mammal.

5. The method of claim 4, wherein said inducible death switch polypeptide is an iCasp9 polypeptide, and said inducing agent is AP1903 or AP20187.

6. The method of claim 4, wherein said vector is administered intramuscularly, and wherein administration of said inducing agent safely reduces said hypoglycemia.

7. The method of claim 1, wherein said insulin polypeptide is a proinsulin polypeptide.

8. The method of claim 1, wherein said insulin polypeptide is a furin-activatable proinsulin polypeptide.

9. The method of claim 1, wherein said inducible death switch polypeptide is an iCasp9 polypeptide.

10. The method of claim 1, wherein said construct comprises an IRES located between said nucleic acid encoding said insulin polypeptide and said nucleic acid encoding an inducible death switch polypeptide.

11. The method of claim 1, wherein said vector is an AAV1 vector.

* * * * *